United States Patent [19]

Brunengraber et al.

[11] Patent Number: 5,667,962
[45] Date of Patent: Sep. 16, 1997

[54] PYRUVATE THIOLESTER FOR THE PREVENTION OF REPERFUSION INJURY

[75] Inventors: Henri Brunengraber, Shaker Heights, Ohio; Hermann Dugas, Montreal, Canada; Khadija Quinze, Villeurbanne, France; Catherine Bomont, Cleveland, Ohio

[73] Assignee: Case Western Reserve University, Cleveland, Ohio

[21] Appl. No.: 617,285

[22] Filed: Mar. 18, 1996

[51] Int. Cl.⁶ .......................... C07C 229/30; A01N 1/02
[52] U.S. Cl. .......................................... 435/1.2; 560/155
[58] Field of Search .................................. 435/1; 560/155

[56] References Cited

U.S. PATENT DOCUMENTS

| | | | |
|---|---|---|---|
| 4,970,143 | 11/1990 | Guidoux et al. | 435/1 |
| 5,075,210 | 12/1991 | Wikman-Coffelt | 435/1 |
| 5,283,260 | 2/1994 | Miller et al. | 514/563 |
| 5,294,641 | 3/1994 | Stanko | 514/540 |

OTHER PUBLICATIONS

Federation Proceedings, vol. 46, No. 7, May, 1987, "Free Radical Scavengers in Myocardial Ischemia", by Paul J. Simpson, et al.

Free Radical Biology & Medicine, vol. XX, No. X, 1995, "Effects of N–Acetylcysteine in the Rat Heart Reperfused After Low–Flow Ischemia: Evidence for a Direct Scavenging of Hydroxyl Radicals and a Nitric Oxide Dependent Increase in Coronary Flow", by Julie Brunet, et al.

Ann. Surg., vol. 209, No. 5, May, 1990, "Effect of Pyruvate on Regional Ventricular Function in Normal and Stunned Myocardium", by mentzer, et al.

Molecular and Cellular Biochemistry, 22: 93–100 "Effect of Pyruvate on Rat Heart Thiol Status During Ischemia and Hypoxia Followed by Reperfusion", By Maria Pia Rigobello and Alberto Bindoli, Jan., 1993.

J. Thorac Cardiovasc Sug., 1991; 101:509–16, "Alcohol and Pyruvate Cardioplegia", by Ann Wikman–Coffelt, et al.

The New England Journal of Medicine, vol. 324, No. 26, "Improvement by Acetylcysteine of Hemodynamics and Oxygen Transport in Fulminant Hepatic Failure", by Phillip Harrison, et al., Jun., 1991.

*Primary Examiner*—Johann Richter
*Assistant Examiner*—Jane C. Oswecki
*Attorney, Agent, or Firm*—Fay, Sharpe, Beall, Fagan, Minnich & McKee

[57] ABSTRACT

The invention comprises a novel pyruvate compound for the treatment or prevention of reperfusion injury following ischemia. The novel pyruvate compound is particularly a pyruvate thiolester. Preferably, the thiol is selected from a cysteine or a methionine amino acid. In a particularly preferred form, the compound is an N-acetyl ethyl ester of the cysteine or methionine amino acid. The most preferred compound is:

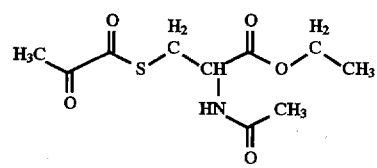

14 Claims, 2 Drawing Sheets

Cardiac Recovery after 25 min. Global Warm Ischemia

PYRUVATE THIOLESTER FOR THE PREVENTION OF REPERFUSION INJURY

BACKGROUND OF THE INVENTION

This invention relates to a new pyruvate compound and a method of treating ischemia in mammalian hearts, lungs, veins, arteries and other organs or tissues. The invention is particularly directed to a method of treating an organ depleted of oxygen with a therapeutic amount of the novel pyruvate compound. The inventive method is especially effective in treating cardiac ischemia and in increasing the viability of transplanted organs.

DESCRIPTION OF THE ART

Ischemia is defined herein as the interruption of oxygen supply, via the blood, to an organ or to part of an organ. Examples of ischemic events include (i) myocardial, cerebral, or intestinal infarction following obstruction of a branch of a coronary, cerebral, or mesenteric artery, and (ii) removal and storage of an organ prior to transplantation. In the case of myocardial infarction, prompt restoration of blood flow to the ischemic myocardium, i.e. coronary reperfusion, is a key component of the treatment. This is because mortality is directly related to infarct size (tissue necrosed) which is related to the severity and duration of the ischemic event.

Notwithstanding the need to supply an organ cut-off from a normal blood supply with oxygen, it has been found that reperfusion injury may occur upon restoration of blood flow. This results from the production of reactive oxygen species (ROS), namely, hydrogen peroxide, hydroxyl radicals and superoxide radicals which are formed from both extracellular and intracellular sources. Particularly, ROS are highly reactive species that, under normal conditions, are scavenged by endogenous defense mechanisms. However, under conditions of post-ischemic oxidative stress, ROS interact with a variety of cellular components, causing peroxidation of lipids, denaturation of proteins, and interstitial matrix damage, resulting in increase of membrane permeability and release of tissue enzymes. In an attempt to minimize these undesirable side effects of perfusion, researchers Simpson, et al., (Free Radical Scavengers and Myocardial Ischemia, *Federation Proceedings*, Volume 46, No. 7 May 15, 1987) suggest the use of an inhibitor of ROS production to protect the reperfused myocardium. Particularly, the Simpson, et al. disclosure is directed to the use of agents and inhibitors (ex. allopurinol) that reduce ROS levels.

In a similar context, Brunet, et al., (Effects of Acetylcysteine, *Free Radical Biology and Medicine*, Volume XX, No. X 1995) suggest the use of acetylcysteine to reperfuse hearts. In particular, the article concludes that acetylcysteine treatment decreases the production of ROS in reperfused rat hearts.

In a further effort directed to protecting reperfused heart tissue, U.S. Pat. No. 5,075,210, herein incorporated by reference, discloses a process for reperfusing a heart for transplantation. The patent discloses a cardioplegic solution containing sodium chloride, potassium chloride, calcium chloride, sodium bicarbonate, sodium EDTA, magnesium chloride, sodium pyruvate and a protein.

U.S. Pat. No. 5,294,641, herein incorporated by reference, is directed to the use of pyruvate to prevent the adverse effects of ischemia. The pyruvate is administered prior to a surgical procedure to increase a patient's cardiac output and heart stroke volume. The pyruvate is administered as a calcium or sodium salt. The pyruvate can alternatively be an ester of pyruvic acid such as ethylamino pyruvate.

Notwithstanding the acceptance of pyruvate as an effective component of a reperfusion solution, it has been recognized that traditional pharmacological pyruvate compounds, such as salts of pyruvic acid, are not particularly physiologically suitable. For example, these compounds lead to the accumulation of large concentrations of ions (ex. calcium or sodium) in the patient's body fluids. Accordingly, while potentially suitable to organ preservation, these pyruvate compounds are less suited to treating a organ in vivo, and it is recognized that a need exists to provide a pyruvate delivery compound which is more physiologically acceptable.

In this regard, U.S. Pat. No. 5,283,260, herein incorporated by reference, is directed to treatment of diabetes with a physiologically acceptable form of pyruvate. The patent discloses a pyruvate compound in the form of a covalently linked pyruvyl-amino acid. By utilizing this type of a pyruvate delivery system, the negative effect of pyruvate salt is avoided. However, administration of large amounts of pyruvate-amino acid may result in nitrogen overload which could harm patients with liver and/or kidney pathology.

Accordingly, it is desirable in this field to have an alternate physiologically compatible therapeutic pyruvate compound.

SUMMARY OF THE INVENTION

Accordingly, it is a primary object of this invention to provide a new and improved pyruvate compound.

It is a further object of this invention to provide a new and improved method for organ reperfusion.

To achieve the foregoing objects and in accordance with the purpose of the invention, as embodied and broadly described herein, the novel pyruvate compound of this invention comprises a pyruvate thiolester. Preferably, the thiol is cysteine or methionine. In a particularly preferred form, the compound is a N-acetyl ethyl ester of the cysteine or methionine amino acid.

The most preferred compound is:

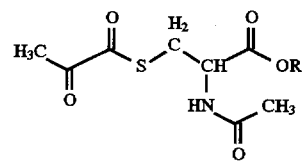

The invention is also directed to use of the novel pyruvate compound in reperfusion of tissue and organs both in vivo and in storage. Accordingly, the invention includes a method for the preservation of tissue deprived of oxygen through events including, but not limited to, coronary infarction, stroke, mesenteric infarction, organ transplant (during preservation and intravenously after grafting of the organ) including amputated limbs. The compound is also believed well suited to treatment of acetaminophen poisoning of the liver which depletes liver glutathione stores leading to acute hepatic necrosis.

It is believed that pyruvate acts as a NADH trap and a trap for ROS generated upon reperfusion. In addition, the thiol group from cysteine, for example is believed to scavenge ROS. Accordingly, the subject novel compound provides a stable, and physiological compound with the beneficial result of delivering pyruvate and a thiol.

BRIEF DESCRIPTION OF THE DRAWINGS

The invention consists of the novel parts, construction and arrangements, combinations and improvements shown and described. The accompanying drawings, which are incorporated in and constitute a part of the specification illustrate one embodiment of the invention and together with the description explain the principals of the invention.
Of the drawings.

DETAILED DESCRIPTION OF THE PREFERRED EMBODIMENTS

Figure 1:
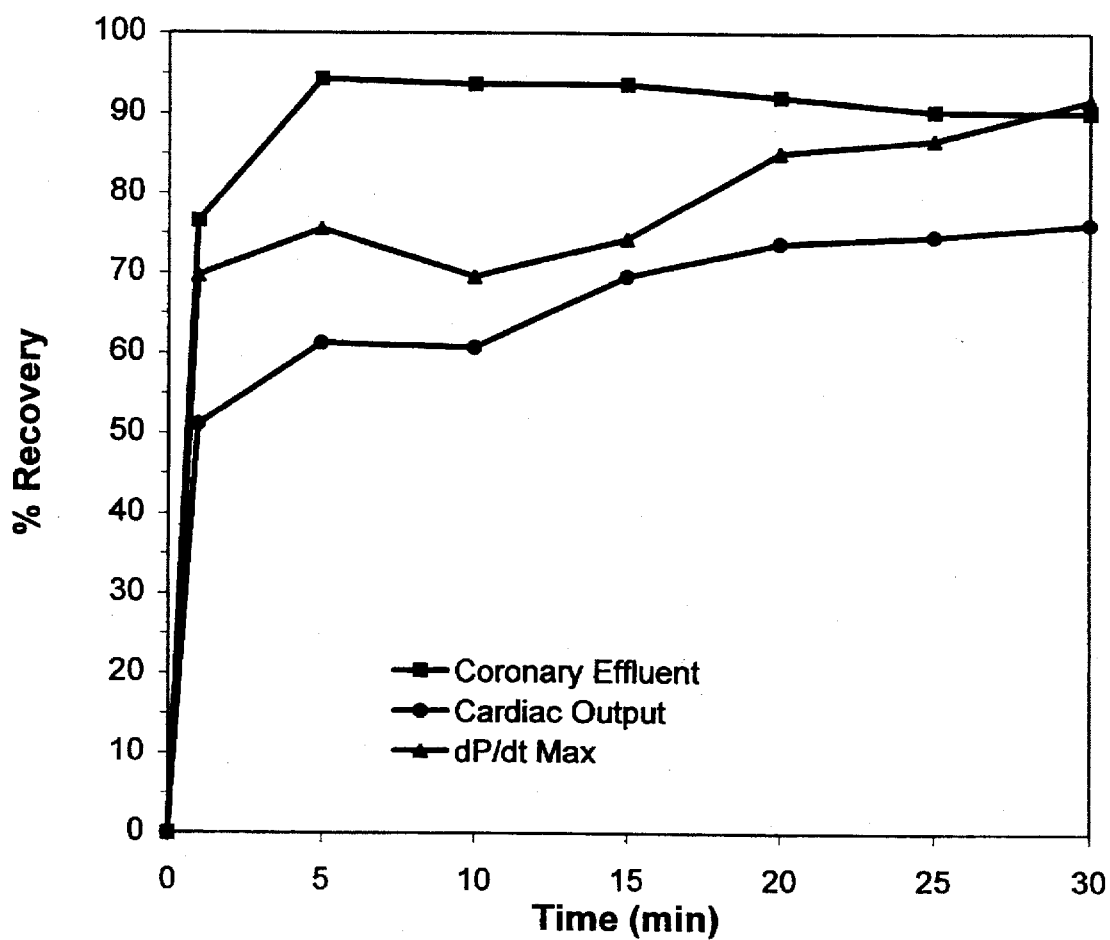
FIGS. 1 and 2 are graphical representations of the results of the experiments set forth hereinbelow.

As described above, timely coronary reperfusion as treatment for acute myocardial infarction reduces myocardial infarct size and improves survival rates. However, there is concern that reperfusion may cause further injury to the myocardium, called "reperfusion injury".

More particularly, experimental studies have demonstrated that myocardium reperfused after reversible ischemia exhibits prolonged depression or "myocardial stunning". There is evidence that reperfusion of ischemic myocardium results in the generation of ROS and that a burst of ROS production at the time of reperfusion causes myocardial damage. Accordingly, attempts have been made to provide pyruvate compounds which trap and/or prevent the formation of ROS.

The present invention is a novel compound including a pyruvate moiety which traps reducing equivalents (NADH) and ROS, and a thiol moiety which traps ROS. Accordingly, the present compound provides dual functionality in an effective and highly efficient manner and in a physiologically soluble molecule. In addition, the compounds are degraded to physiological and safe metabolites (pyruvate, cysteine or methionine). Lastly, the present inventive compound is equally applicable to use in the preservation of organs removed for transplantation.

The novel compounds are redox chimeras whose molecules contain a trap for reducing equivalents (NADH) and a trap for ROS.

The inventive compounds demonstrate the following characteristics;

(i) water solubility;
(ii) no ionic charge, to facilitate diffusion through cell membranes and to avoid the need to administer a counter-ion, such as $Na^+$;
(iii) metabolizable to physiological compounds; and
(iv) stability in solution.

The compounds are generally a thiolester of pyruvate and a sulfur amino acid, for example cysteine and/or methionine. Preferably, any ionizable functions on the amino acid molecule are blocked by easily removable radicals, such as ethyl and N-acetyl groups. The most preferred compound is formed of pyruvate and N-acetylcysteine ethyl ester.

The invention will now be described with reference to the following examples, intended to describe, but not limit the invention.

Recovery of isolated rabbit hearts following 25 min of warm ischemia

Hearts were removed from anesthetized New Zealand rabbits (2.5-3.0 kg) and perfused in the working mode at 37° with non-recirculating Krebs-Ringer bicarbonate (KRB) buffer containing 5 mM glucose and 5 Units/l of insulin, and equilibrated with a gas mixture containing 95% $O_2$+5% $CO_2$. In the working mode, which simulates physiological conditions, hearts pump the buffer against a 85 cm hydrostatic pressure in the aorta. The mechanical performance of the hearts was assessed by monitoring heart rate, cardiac output, coronary flow, left ventricular pressure, and $dP/dt_{max}$. The latter parameter reflects the capacity of the heart to increase hydrostatic pressure in the left ventricle.

Following 30 minutes of equilibration, the hearts were made ischemic for 25 minutes by clamping the aortic and left atrial canulas. Then, the clamps were removed to allow reperfusion with oxygenated KRB buffer containing either no additive (n=7, control group), or 20 µM pyruvate-N-acetyl-cysteine ethyl ester (PNACE) (n=7). PNACE was infused via a syringe pump into the inflowing perfusate. In the syringe, PNACE was dissolved in 0.1 mM HCl to prevent hydrolysis of the thiolester.

None of the control group hearts recovered any function. In contrast, hearts reperfused with buffer containing 20 µM PNACE recovered 75 to 95% of their mechanical function after reperfusion was instituted (see FIGS. 1 and 2). Functional recovery lasted throughout the 30 minute reperfusion experiment.

Recovery of isolated rabbit hearts following massive catecholamine injury

Rabbit hearts were perfused in the working mode as in the above example. However, after the 30 minutes of equilibration, 50 µM isoproterenol was added to the inflowing perfusate for 10 min. Isoproterenol is a catecholamine, which, at the dose administered, induces a marked increase in heart rate and cardiac output. After 10 minutes, the mechanical performance of the hearts decreased markedly to the point where cardiac output was almost zero. Then, isoproterenol infusion was stopped, and perfusion was continued for 30 minutes with oxygenated KRB buffer containing either no additive (n=7, control group), or 20 µM PNACE (n=7). The hearts perfused with plain buffer did not show recovery of cardiac function. In contrast, hearts perfused with buffer containing 20 µM PNACE recovered 75 to 95% of their mechanical function.

Figure 2:
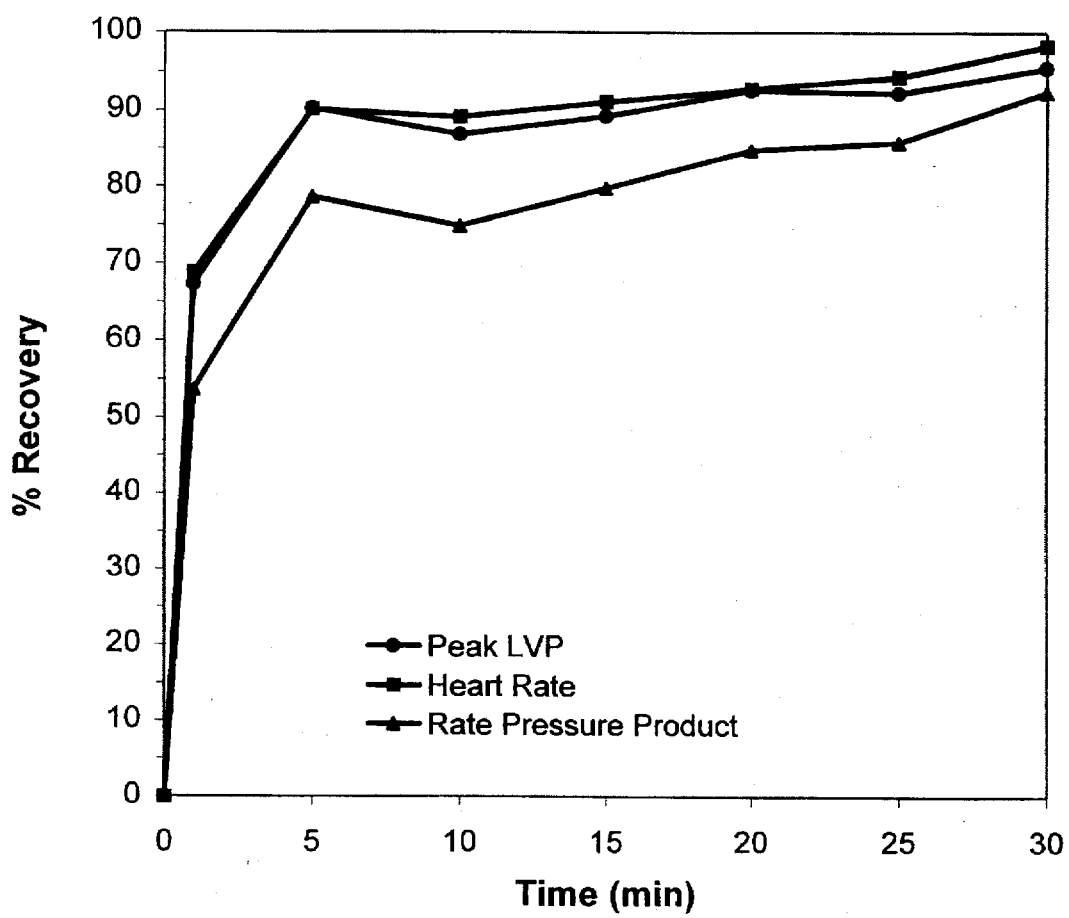

The data of these experiments proved substantially similar to that shown in FIGS. 1 and 2.

Improved function of preserved rat livers

Livers from overnight-fasted rats were surgically removed and flushed at 37° C. with non-recirculating KRB buffer containing 5 mM glucose and equilibrated with a gas mixture containing 95% $O_2$+5% $CO_2$. The first group of livers (n=7, control group) was not preserved, but was perfused at 37° C. for 45 minutes. The second group of livers (n=8, preserved group) was flushed with ice-cold University of Wisconsin (UW) preservation solution and stored for 24 hours in ice-cold UW solution. Next, the livers were reperfused at 37° C. with non-recirculating KRB buffer containing 5 mM glucose. The third group of livers (n=8, preserved+PNACE group) was treated as the second group except that 20 µM PNACE was added to the UW preservation solution and to the reperfusion KRB buffer. During the last 45 min of (re)perfusion, the function of the three groups of livers was assessed by (i) the release of three cellular enzymes, i.e. lactate dehydrogenase, aspartate aminotransferase, and alanine aminotransferase, (ii) oxygen consumption, and (iii) the production of ketone bodies, ie β-hydroxybutyrate+acetoacetate, after addition of 1 mM octanoate to the perfusate.

The data depicted in the Table, show that, in preserved reperfused rat livers, PNACE (i) markedly decreases the initial release of tissue enzymes, (ii) restores partially the capacity of the liver to oxidize fatty acids to ketone bodies, and (iii) restores oxygen consumption to the level of non-preserved livers.

Effect of PNACE on metabolic integrity of preserved
rat livers upon reperfusion
All data from group III are statistically different from
the corresponding data of group II.

| Parameter measured | Group I Control non-preserved (7) | Group II Control preserved (8) | Group III Preserved + PNACE (8) |
|---|---|---|---|
| Release of lactate dehydrogenase (U/L.g) 10–14 min. | 1.9 | 21.8 | 4.5 |
| Release of aspartate amino-transferase (U/L.g) 25–30 min. | 0.28 | 3.4 | 0.73 |
| Release of alanine aminotransferase (U/L.g) 25–30 min. | 0.21 | 3.7 | 0.33 |
| Ketone body production (µmol/min.g) 25–30 min. | 3.1 | 0.9 | 1.4 |
| Oxygen consumption (µmol/min.g) 25–30 min. | 2.1 | 1.3 | 2.4 |

As understood in the art, pyruvate has proven to be a relatively unstable compound with very limited mechanism for satisfactory delivery to subjects. However, the present inventive compound has proven to be readily manufacturable and very effective in the prevention of organ damage associated with reperfusion injury. The compound has been prepared in pure form and in gram amounts. Its formula has been confirmed by elemental analysis and gas chromatography-mass spectrometry. The compound is stable in slightly acidic solutions (pH 4–5). At pH 7.4, it is slowly hydrolyzed to pyruvate and N-acetylcysteine ethyl ester. The compound has also been synthesized labeled with three deuterium $^2H$ atoms on the N-acetyl moiety. This deuterated compound is used as an internal standard for the assay of the compound by isotope dilution gas chromatography-mass spectrometry.

Synthesis of PNACE

In a three-neck flask of 500 ml, freshly distilled pyruvic acid (9.06 g., 0.102 mol) and N-hydroxy-succinimide (11.82 g., 0.102 mol) in dry tetrahydrofurane (THF) (180 ml) was stirred under nitrogen and was cooled in a ice bath. Dicyclohexylcarbodiimide (21.2 g., 0.102 mol) dissolved in dry THF (150 ml) was added slowly to the stirred cooled mixture over approximately 1 hr. Then, the reaction mixture was stirred at room temperature for 2.5 hr, followed by slow addition of N-acetyl-L-cysteine ethyl ester (6.81 g., 0.033 mol) dissolved in 20 ml dry THF over approximately 1 hr.

The reaction mixture was stirred overnight at room temperature under a nitrogen atmosphere.

After evaporating the THF, the residue was suspended in ethyl acetate (750 ml) and was kept for 4–6 hr at 0° C. Dicyclohexyl urea (DCU) was then filtered and discarded; the ethyl acetate solution was washed three times with water (3×100 ml). It was then dried over anhydrous sodium sulfate and concentrated under vacuum.

The product (17–18 g.) was further purified by using column chromatography. A column of 5 cm. diameter was filled with silica gel (180–200 g., 60 Angstrom flash chromatography from Aldrich). The product was dissolved first in a minimum quantity of ethyl acetate:hexane (60:40) and was loaded on the column. The column was developed under gravity (rather than flash chromatography) with ethyl acetate:hexane (60:40). Fifty ml fractions were collected and monitored by TLC using either iodine or UV light. The fractions containing the product were combined and solvents were removed under reduced pressure. The residue was dissolved in chloroform (300 ml), first washed with 5% HCl (2×30 ml) and then saturated NaCl (3×60 ml). The organic layer was dried over anhydrous sodium sulfate, filtered, and the solvent evaporated. The residue was dissolved in a minimum quantity of chloroform, and petroleum ether was added until the solution became turbid. The suspension was kept overnight in the refrigerator and then filtered to get the pure crystallized product. The compound was dried under vacuum over $P_2O_5$ to a yield of 6.5 g. (75%, based on the N-acetyl-L-cysteine), m.p. 76°–77° C.

Alternative Synthesis of PNACE

To a 250 ml three neck flask fitted with a thermometer, a magnetic stirrer, a 50-ml pressure-compensated addition funnel, and a Friedrich's condenser under nitrogen, was added 10 g (52.3 mmoles) of N-acetyl-L-cysteine ethyl ester, 8.0 ml of dry pyridine and 60 ml of dry benzene.

Pyruvoyl chloride (0.104 mole, 2 eq) was added dropwise over a period of 0.5 hr. while maintaining a temperature of 5° C. to 10° C. Then, the reaction mixture was allowed to warm to 25° C. and stirred for 2 hours at this temperature. The benzene solvent was then evaporated under vacuum. The crude product was purified as above to yield 11.15 g of the desired compound (82%).

Synthesis of Deuterated PNACE

Pyruvate-N-[$^2H_3$]acetyl-L-cysteine ethyl ester

Synthesized wherein the above procedure was followed using N-[$^2H_3$] acetyl-L-cysteine ethyl ester to form ($d_3$-PNACE). The latter was prepared by reacting L-cysteine ethyl ester with [$^2H_6$]acetic anhydride.

Set forth hereinbelow are certain analytical characteristics of the composition of the invention provided to facilitate identification thereof, but not intended to limit the scope.

CHARACTERISTICS OF COMPOUNDS

I. Pyruvate-N-acetyl-L-cysteine ethyl ester : PNACE (unlabeled)

mp: 65° C.
Rf (ethyl acetate/petroleum ether: 3/2) : 0.52
IR (Nicolet 300, $CCl_4$) ($cm^{-1}$):
3435 (V N—H)
3000 (v C—H)
1747 (v CO—O) ester
1731 (v CO—S) thioester
1687 (v CO—CO,CO—N) ketoester, amide
1497, 1378.3, 1210.1
NMR $^1H$, 300MHz (Varian, $CDCl_3$, TMS) (ppm): NMR $^{13}C$, 100.12 MHz (Bruker, $CDCl_3$, TMS) (ppm):
1.33 (t, $^3J$=7.13, 3H, $OCH_2CH_3$)     190.6; 188.08 keto, ketoester

CHARACTERISTICS OF COMPOUNDS

| | |
|---|---|
| 2.10 (s, 3H, COCH$_3$) | 168.6, 168.08 ester, amide |
| 2.50 (s, 3H, CH$_3$COCO) | 60.1 (OCH$_2$) |
| 3.45 (dd, $^3$J=4.10 Hz, $^3$J=8.95 Hz, 2H, CH$_2$—S) | 49.5 (CH$_2$S) |
| 4.23 (dd, $^3$J=7.13 Hz, 2H, CH$_2$CH$_3$) | 28.4 (CHNH) |
| 4.83 (m, 1H, CH) | 21.9 (CH$_3$COCO) |
| 6.50 (sl, 1H, NH) | 20.8 (CH$_3$CO) |
| | 12.1 (CH$_3$CH$_2$) |
| Mass spectrum, electron ionization (m/z): | Mass spectrum, ammonia chemical ionization (m/z): |
| 190 (M − CH$_3$COCO,33); 118 (26); | 279 (M + 18,100); 262 (M + 1, 93); 209 (49); 192 (60) |
| 102 (56); 76 (33), 60 (90), 43 (CH$_3$CO$^+$, 100) | 175 (18), 158 (26) |
| II. Pyruvate-N-[$^2$H$_3$]acetyl-L-cysteine ethyl ester: d$_3$-PNACE (deuterated) | |
| NMR $^1$H, 300Mhz (Varian, CDCl$_3$, TMS) (ppm): | NMR $^{13}$C, 100 MHz (Bruker, CDCl$_3$, TMS) (ppm): |
| 1.34 (t, $^3$J=7.13, 3H, OCH$_2$CH$_3$) | 190.5; 187.08 keto, ketoester |
| 2.50 (s, 3H, CH$_3$COCO) | 168.5, 168.10 ester, amide |
| 3.42 (dd, $^3$J=4.10Hz, $^3$J=8.95Hz, 2H, CH$_2$—S) | 60.1 (OCH$_2$) |
| 4.25 (dd, $^3$J=7.13Hz, 2H, CH$_2$CH$_3$) | 49.1 (CH$_2$S) |
| 4.90 (m, 1H, CH) | 28.1 (CHNH) |
| 6.50 (sl, 1H, NH) | 20.8 (CH$_3$COCO) |
| | 19.9 (CD$_3$CO) |
| | 12.0 (CH$_3$CH$_2$) |
| Mass spectrum, electron ionization (m/z): | Mass spectrum, ammonia chemical ionization (m/z) |
| 193 (M − CH$_3$COCO, 17); 121 (4);103 (29); | 282(M + 18, 42); 265 (M + 1, 47); 212 (23), |
| 77 (12); 63 (26); 43 (CH$_3$CO, 100) | 195 (37); 178 (53); 161 (100); 106 (23); |
| | 89 (15). |

Thus it is apparent that there has been provided, in accordance with the invention, a novel pyruvate compound and a method of treating ischemia that fully satisfies the objects, aims and advantages set forth above. While the invention has been described in conjunction with specific embodiments thereof, it is evident that many alternatives, modifications, and variations will be apparent to those skilled in the art in light of the foregoing description. Accordingly, it is intended to raise all such alternatives, modifications and variations as fall within the spirit and broad scope of the appended claims.

What is claimed:

1. A process for preserving tissue deprived of oxygen comprising the step of treating said tissue with an effective amount of a pyruvate thiolester.

2. The process of claim 1, wherein said thiolester is cysteine.

3. The process of claim 2, wherein said thiolester is a N-acetylcysteine.

4. The process of claim 1 wherein said tissue comprises organs removed from a living organism and said step of treating comprises perfusing said organ with a solution containing said pyruvate thiolester.

5. The process of claim 1, wherein said solution contains a pyruvate thiol ethyl ester.

6. The process of claim 5, wherein said thiolester is cysteine.

7. The process of claim 6, wherein said thiolester is a N-acetylcysteine.

8. The process of claim 4, wherein said solution contains a pyruvate thiol ethyl ester.

9. The process of claim 4, wherein said solution further comprises a physiological electrolyte component.

10. The process of claim 1 wherein said tissue comprises human cardiac muscle and said step of treating comprises administering to said human, orally, intravenously, or intra-coronaryly an effective dosage of said pyruvate thiolester to increase the cardiac output of a human.

11. The process of claim 10, wherein said thiolester is cysteine.

12. The process of claim 11, wherein said thiolester is a N-acetylcysteine.

13. The process of claim 10, wherein said compound is a pyruvate thiol ethyl ester.

14. The process of claim 10, wherein said pyruvate thiolester is

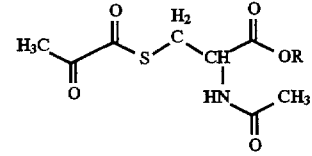

wherein R is selected from ethyl, methyl and alkyl groups.

* * * * *